United States Patent [19]
Blackwell

[11] Patent Number: 5,951,459
[45] Date of Patent: Sep. 14, 1999

[54] MAGNETIC COIL FOR PULSED ELECTROMAGNETIC FIELD

[75] Inventor: Lyman L. Blackwell, Tubac, Ariz.

[73] Assignee: Orthosoft, L.L.C., Tucson, Ariz.

[21] Appl. No.: 08/920,870

[22] Filed: Aug. 29, 1997

[51] Int. Cl.[6] .................................................. A61N 1/00
[52] U.S. Cl. ............................................ 600/13; 600/15
[58] Field of Search .......................................... 600/9–15

[56] References Cited

U.S. PATENT DOCUMENTS

| | | |
|---|---|---|
| 4,105,017 | 8/1978 | Ryaby et al. . |
| 5,181,902 | 1/1993 | Erickson et al. . |
| 5,192,263 | 3/1993 | Kraus . |
| 5,195,940 | 3/1993 | Baylink . |
| 5,195,941 | 3/1993 | Erickson et al. . |
| 5,267,939 | 12/1993 | Liboff et al. . |
| 5,269,745 | 12/1993 | Liboff et al. . |
| 5,290,409 | 3/1994 | Liboff et al. . |
| 5,312,534 | 5/1994 | Liboff et al. . |
| 5,314,401 | 5/1994 | Tepper . |
| 5,316,634 | 5/1994 | McLeod . |
| 5,318,561 | 6/1994 | McLeod et al. . |
| 5,330,410 | 7/1994 | Baylink . |
| 5,338,286 | 8/1994 | Abbott et al. . |
| 5,376,245 | 12/1994 | McLeod . |
| 5,415,617 | 5/1995 | Kraus . |
| 5,458,558 | 10/1995 | Liboff et al. . |
| 5,743,844 | 4/1998 | Tepper et al. . |

OTHER PUBLICATIONS

Ruibal, S., "Ironclad Cures For Pain? Athletes Put Their Faith In Power Of Magnets," *USA Today*, Aug. 20, 1997, p. 3C.

*Primary Examiner*—John P. Lacyk
*Attorney, Agent, or Firm*—Hunton & Williams

[57] ABSTRACT

A portable electronic PEMF apparatus comprises a PEMF coil, power supply, and electronic switching means contained therein. The power supply along with the switching means provide periodic electric power to the PEMF coil. The PEMF coil comprises multiple turns of a conductive wire around a core with an elongated cross section. The core comprises a magnetic shield layer of materials such as mu metal or soft iron. The power supply comprises a battery, a regulated voltage source and unregulated voltage source from the battery and electronic switching circuit, powered by the regulated voltage, for electrically connecting the unregulated voltage source to the coil. The electronic switching circuit is tuned to periodically provide power to the coil at a frequency to generate a non-inverting, varying electromagnetic field from the coil.

23 Claims, 5 Drawing Sheets

MAGNETIC COIL FOR PULSED ELECTROMAGNETIC FIELD

FIELD OF THE INVENTION

The present invention generally relates to pulsed electromagnetic field (PEMF) coils for the treatment of injuries in a patient, and more specifically to methods and apparatuses relating to portable PEMF coils, and PEMF coils with high field strength and field generating efficiency.

BACKGROUND OF THE INVENTION

Traditional methods for treating certain injuries to a body (e.g., humans, animals) involve setting and immobilize the injured member to allow natural healing of the injury. Often, it is desirable that natural healing will restore damaged structures to their original uninjured condition without significant inconvenience to a patient. Traditional problems in injury treatments have been associated with the inability of the patient's body to heal correctly or rapidly and the inability of the healed part to regain fall strength and freedom of movement. These problems are especially acute in patients with suboptimal health and reduced healing capacity such as elderly, bedridden or patients with multiple disorders.

Attempts to address these problems and to promote more rapid healing have led to the use of pulsed electromagnetic fields. It is generally known that electromagnetic fields applied to a body can produce favorable biological effects. For example, FDA approved pulsed electromagnetic field (PEMF) apparatuses are available for use in bone healing. These apparatuses are used to augment and accelerate the natural healing process. PEMF is also effective in the treatment of severe injuries and fractures which are not otherwise treatable using conventional techniques.

Known methods and apparatuses which have been used to treat injuries using PEMF include the use of Helmholtz and toroidal coils to deliver PEMF. These methods and apparatuses have suffered from various deficiencies. For example, Helmholtz coils suffer from field inhomogeneity and field dropouts (e.g., the field drops to zero near the center of the coil). Toroidal coils are inefficient and have a relatively weak field strength. Further, known methods of PEMF treatment have problems associated with system complexity, large size and weight, long treatment times, weak PEMF strength and low efficiencies in promoting healing. Current devices and methods of PEMF treatment further fail to provide adequate mobility during treatment. Other drawbacks also exist.

SUMMARY OF THE INVENTION

It is an object of the present invention to overcome these and other drawbacks of the prior art.

It is another object of the present invention to provide a PEMF apparatus using a coil design that produces a single polarity magnetic field that is relatively homogenous and that maintains its field strength even at distances spaced from the coil.

It is another object of the present invention to provide a PEMF apparatus using a planar coil with a core comprising a magnetic shielding material.

It is another object of the present invention to provide a PEMF apparatus sized to allow PEMF treatment while a patient is mobile and engaged in physical activity.

It is another object of the present invention to provide a PEMF apparatus which can be incorporated as part of a cast or attached to the outside of a cast to augment the natural healing abilities of the body.

It is another object of the present invention to provide an efficient method to energize a coil to produce a single polarity PEMF that eliminates or minimizes ringing without the need for a shunt diode across the coil.

It is another object of the present invention to provide a coil for use in PEMF treatment which is deformable, flexible and pliant and easily adaptable for the application of an electromagnetic field to injuries at any location on a patient's body.

To accomplish these and other objects of the present invention, one preferred embodiment of the invention is directed to a PEMF apparatus having a coil wrapped around a core in a generally rectangular configuration with a magnetic shield located within the core. The coil comprises a plurality of turns of an electrically conductive wire, preferably with each turn having at least two dimensions wherein a first dimension is at least 5 times as great as a second dimension. The apparatus may be deformable, flexible and pliant, and may be shaped to conform to portions of a patient's body. Advantageously, both the top and bottom surfaces of the apparatus will produce a substantially homogeneous, unipolar, non-inverting PEMF with little or no field dropout. The top and the bottom surface generate PEMF of opposite polarity. Preferably the surface generating the N polarity of the magnetic field may be positioned proximal to the portion of the patient to be treated.

According to another preferred embodiment, the core comprises a first end portion and a second end portion of a spacer material such as wood, plastic, foam, or other material which defines a width, height and thickness. The first and second end portions may be separated by a space therebetween. A sheet of magnetic shielding material such as metal is wrapped around the first and second end portions to define a core with an inner surface and a top surface. A plurality of turns of an electrically conductive wire may be wound around the first end portion, the bottom surface, the second end portion and the top surface to form a coil. The components of the core may be attached to each other and to the coil by adhesives such as epoxy.

According to another preferred embodiment, a PEMF treatment apparatus for PEMF treatment of a patient while the patient is engaged in active physical activity is disclosed. The PEMF treatment apparatus preferably comprises a coil wrapped around a flexible core, a power supply and a solid state switching circuit connected between the power supply and the coil to drive the coil with a current at a periodic pulsed frequency to generate a non-inverting PEMF. The power supply is preferably a battery.

Other embodiments and advantages of the invention are set forth in the description taken in conjunction with the drawing figures.

DETAILED DESCRIPTION OF THE PREFERRED EMBODIMENTS

Figure 1A:
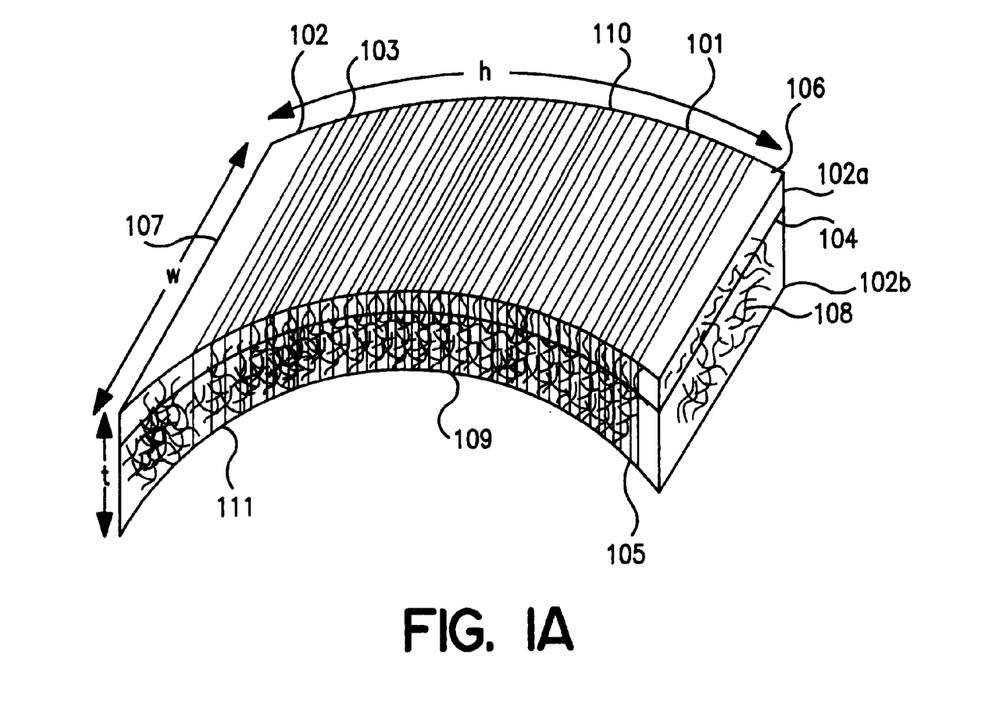
FIG. 1A is a schematic illustration of one preferred embodiment of a PEMF coil assembly.

FIG. 1A illustrates a coil assembly for use with a PEMF apparatus according to one preferred embodiment. The coil assembly 101 comprises a core 102 and a coil 103. The core 102 preferably is generally rectangular with a predetermined thickness and comprises a magnetic shielding material 104. However, other shapes may be used. According to one embodiment, the magnetic shielding material 104 is preferably sandwiched between two sections (102a, 102b) of the core 102. The core 102 is preferably made from a deformable, flexible and/or pliant material such as neoprene or the like which can be easily molded to a portion of a body. The core 102 has a bottom surface 105 and a top surface 106 defining a thickness t, a first side edge portion 107 and a second side edge portion 108 defining a height h, and a first end portion 109 and a second end portion 110 defining a width w. An electrically conductive wire 111 is wound a plurality of turns around the first end portion 109, the bottom surface 105, the second end portion 110, and the top surface 106 to form coil 103. Using the coil assembly 101, a pulsed electromagnetic field which does not suffer from deficiencies characteristic of prior art coils may be generated for the treatment of patients. Deficiencies of prior art coils, like the Helmholtz coil, include field inhomogeneity, field inversion and field dropout. The PEMF generated by coil assembly 101 is substantially uniform in field strength, substantially of one polarity, and comprises little or no field dropout. When driven at the same power level, the field strength of the coil assembly 101 can be stronger than prior art PEMF coils. The stronger homogeneous field strength that can be generated by coil assembly 101 contributes to more therapeutic and effective PEMF treatment.

Figure 1B:
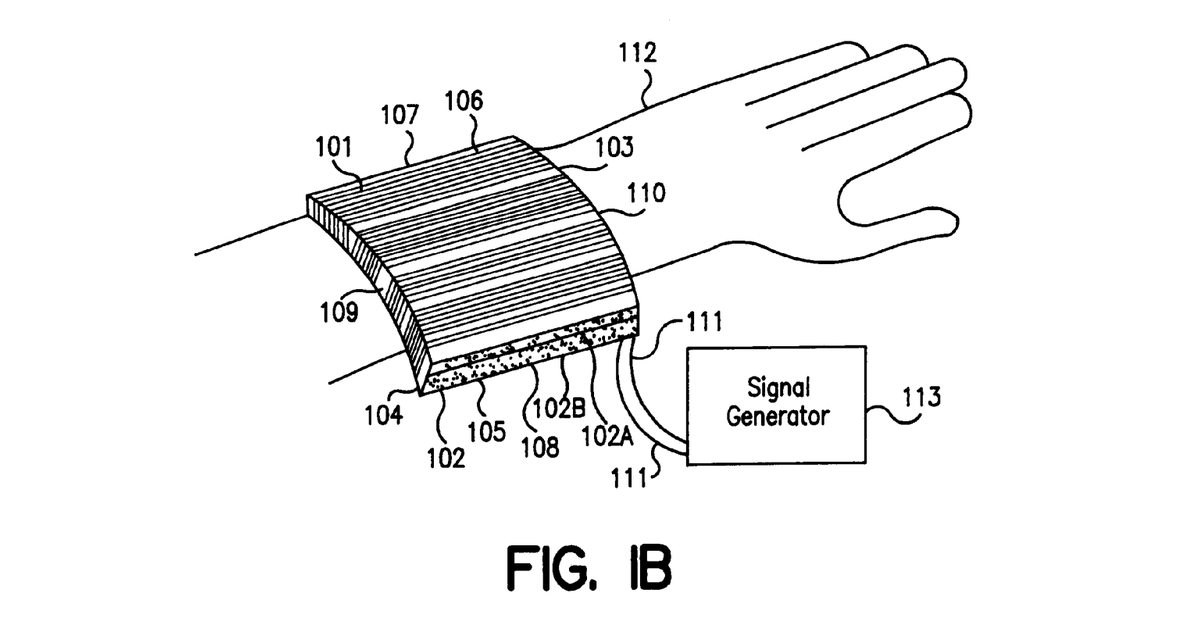
FIG. 1B is a schematic illustration of a PEMF apparatus using a PEMF coil assembly in the treatment of a hand.

FIG. 1B illustrates the operation of a coil assembly 101 for the treatment of a hand 112 of a patient. The coil assembly 101 is positioned adjacent the hand 112. A signal generator 113 is connected to electrically conductive wires 111 of the coil assembly 101. A periodic electric current, supplied by the signal generator 113, is applied through electrically conductive wires 111 to coil assembly 101 to generate a PEMF.

Figure 2A:
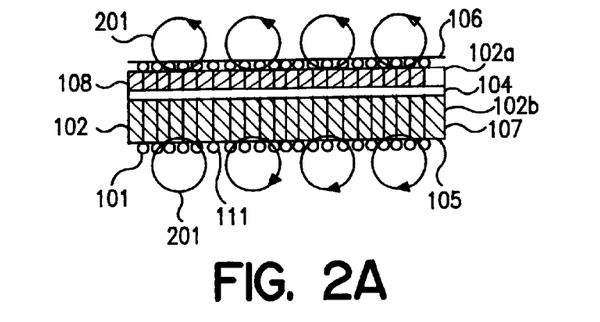
FIG. 2A is a cross section through the thickness of a PEMF coil assembly, according to one embodiment of the invention, showing magnetic flux lines.
Figure 2B:
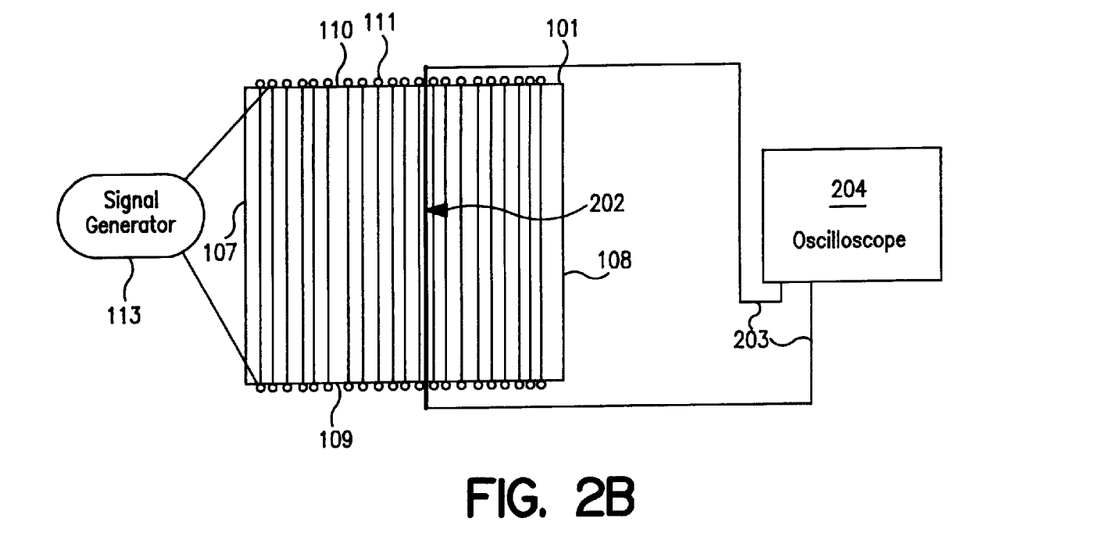
FIG. 2B illustrates the measurement of an energized PEMF coil using an oscilloscope.
Figure 2C:
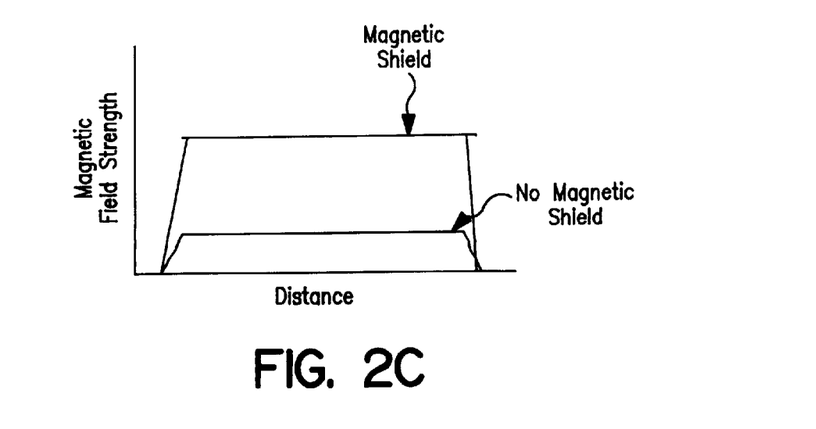
FIG. 2C is a graph of magnetic field strength vs. distance of one embodiment of a PEMF coil both with and without a metallic shielding material as measured by a straight sensing wire according to the configuration of FIG. 2B.

FIG. 2A is a cross-sectional view of a preferred embodiment of a coil assembly 101 showing a representation of the PEMF lines 201. The field generated by the coil 103 may be measured using a wire sensor 202 (FIG. 2B). The PEMF field induces a current into the wire sensor 202. The wire sensor 202 is connected by wires 203 to an oscilloscope 204 or other measuring device. The single wire sensor 202 is more representative of bone or tissue than a pick-up sensing coil of the type commonly used. Using the wire sensor 202, PEMF strength is measured as a function of distance along the coil assembly 101. These field strength measurements are made with and without magnetic shielding material 104 within the coil. Representative measurements are shown in FIG. 2C. Comparison of PEMF strength between similar coil assemblies with and without magnetic shielding material 104 shows that the magnetic shielding material 104 can increase the PEMF strength by about three fold (FIG. 2C).

Figure 3:
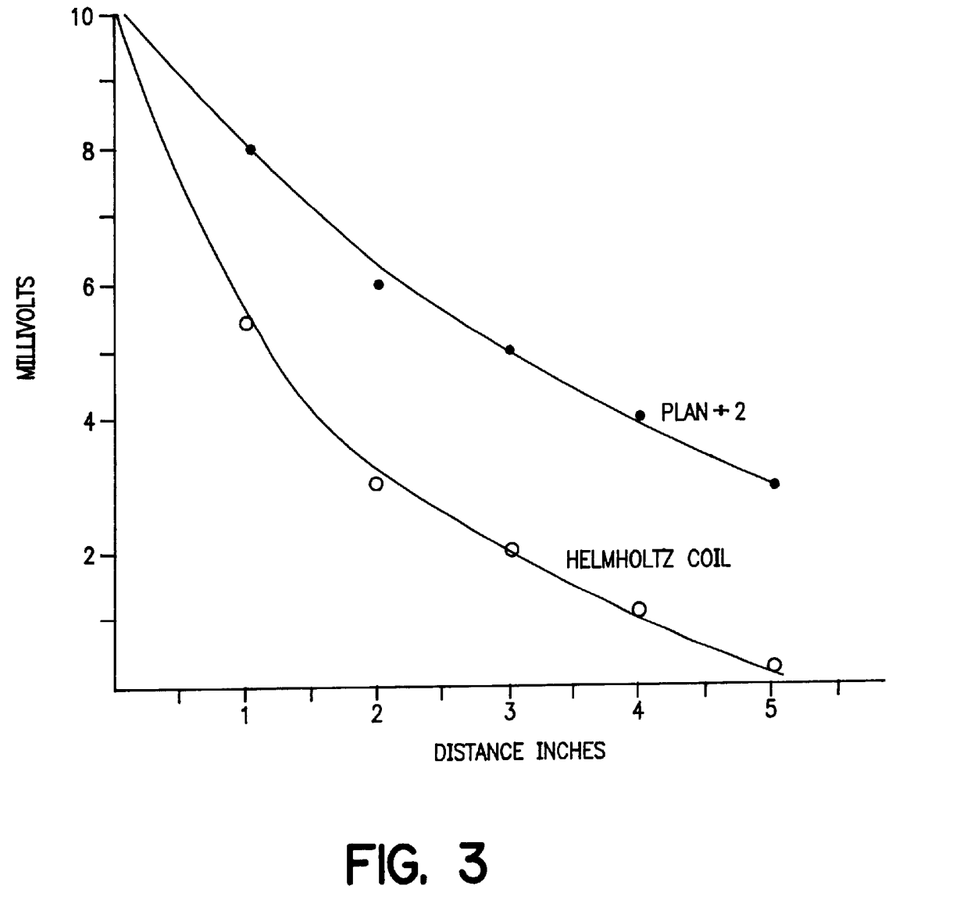
FIG. 3 is a graph of voltage (mv) vs. distance (in.) for a PEMF coil assembly and a Helmholtz coil assembly.

FIG. 3 illustrates a plot of PEMF strength as a function of normal distance from a planar coil and a Helmholtz coil. PEMF from a planar coil assembly according to the present invention shows increased field strength compared to Helmholtz coils at all distances measured.

Figure 4A:
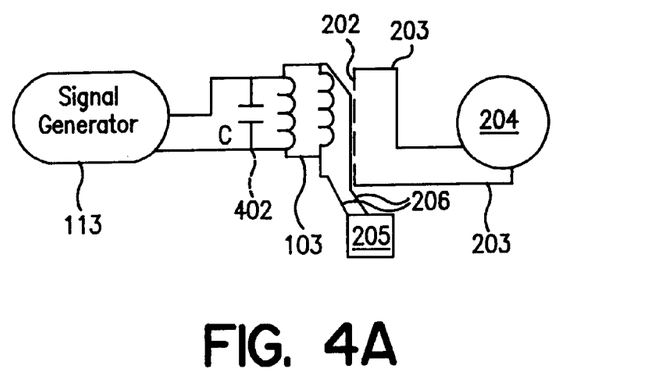
FIG. 4A is a schematic illustration of one implementation of a PEMF coil apparatus according to the present invention.

FIG. 4A illustrates an electrical schematic of one preferred embodiment of the PEMF coil assembly 101. Coil 103 is connected in parallel with capacitor 402 to achieve a high Q resonance circuit. The coil 103 and capacitor 402 are driven by signal generator 113. Voltage across the coil 103 is measured by an oscilloscope 205 (or other measuring device) through wires 206. The PEMF generated from the coil 103 is measured by wire sensor 202 which is connected to oscilloscope 204 by wires 203.

Figure 4B:
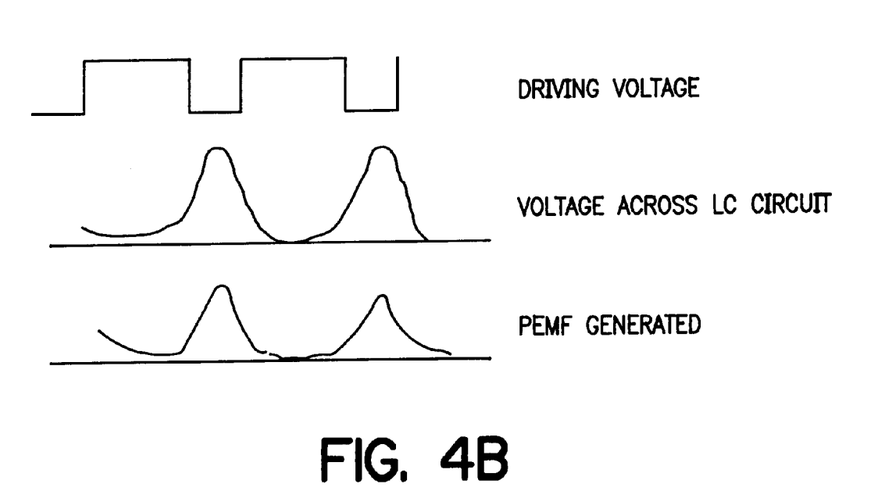
FIG. 4B is a schematic illustration of a PEMF driving voltage, a measured voltage and a PEMF with no voltage inversion according to one aspect of the invention.
Figure 4C:
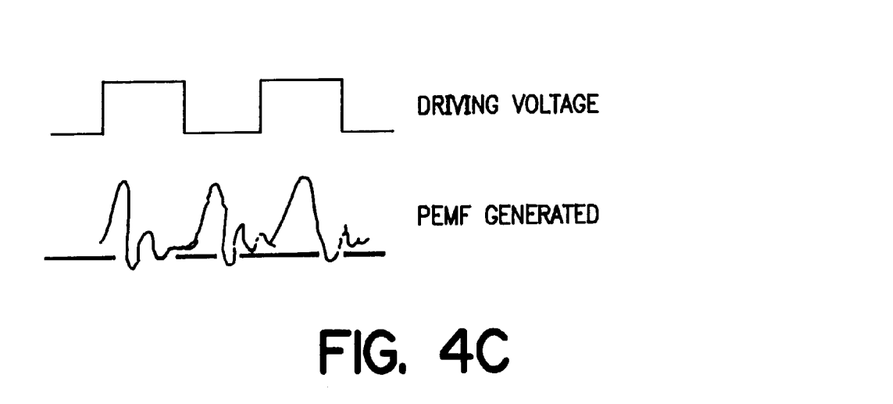
FIG. 4C is a schematic illustration of a driving voltage and PEMF measurement according to another device.

FIG. 4B illustrates the behavior of the PEMF coil assembly 101 driven by a periodic electric current of 10 volts at a duty cycle of about 1.0 milliseconds to about 4 milliseconds on and about 2 to about 3 milliseconds off. The voltage across a coil 103 driven by the periodic electric current was measured by an oscilloscope 205 and plotted on FIG. 4B. The voltage across the coil is non-inverting with a peak of about 80 volts. The PEMF generated by the planar coil was measured by the wire sensor 202, plotted by oscilloscope 204 and shown to be non-inverting (FIG. 4B). In contrast, if the duty cycle of the periodic electric current was altered to 1 msec on, 1 msec off, the resulting PEMF will have an undesired wave component as shown in FIG. 4C.

Figure 5:
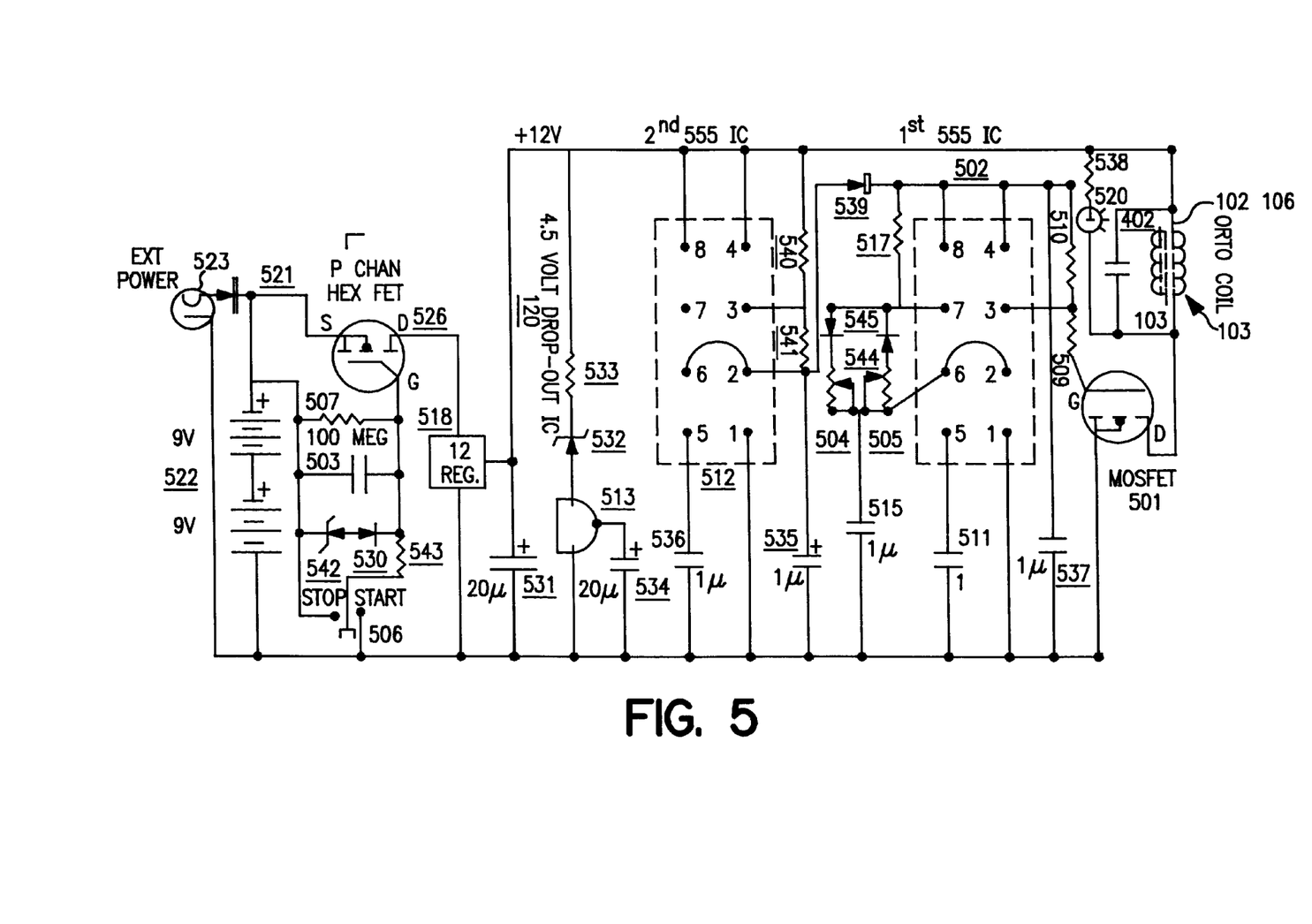
FIG. 5 is an electrical schematic showing one implementation of a solid state switching circuit according to one embodiment of the invention.

FIG. 5 illustrates an electrical schematic of one preferred embodiment of a solid state switching circuit. Coil 103 is connected in parallel to capacitor 402 to generate a circuit with a desirable Q factor. Power to the coil 103 and capacitor 402 is regulated by transistor 501—Transistor 501 is regulated by oscillator 502 to deliver a periodic electric current to capacitor 402 and coil 103. The frequency of the oscillator 502 in turn is regulated by potentiometers 504 and 505, resistors 509, 510 and 517, diodes 544 and 545 and capacitors 511 and 515 connected as shown in FIG. 5. Oscillator 512 regulates the delivery of PEMF in timed intervals. A timed interval of, for example, ½ second of PEMF treatment and ½ seconds of no PEMF treatment is preferred. However, other on and off times may be used. The duty cycle of oscillator 512 is controlled by resistors 540 and 541, and capacitors 535 and 536. Regulated power for both oscillators is preferably supplied by a voltage regulator 518. Further a LED 520 may optionally be included to in form users that PEMF is applied. Electrical power is preferably supplied to this PEMF coil by battery 522 or by an external DC source via socket 523.

The preferred embodiment of the invention is directed to a PEMF apparatus comprising one or more planar coils. The construction of one preferred apparatus will now be described.

Planar Core

The core 102 may be generally rectangular or curved. Curved cores may comprise shapes such as a convex, concave, saddle shaped, or any other shape that can proximate the body or body portion for which the coil will be used. For example, a coil designed to treat shoulder injuries may have a surface which is similar to the exterior surface of the shoulder.

The core 102 may comprise an insulating material such as a polymeric or foam material, an elastomer, air or a physical blend of such materials and the like. Examples of polymeric materials may comprise plastics, polymers, and resins such as, for example, celluloid, phenolic plastics, and thermoset plastics. Foams may comprise any material with a sponge like cellular structure such as sponge rubber, plastic foams, urethane foam, phenolic foam, and cellulose foam. Elastomers may comprise, for example, rubber, tryene-butadiene, neoprene, isoprene and celluloid. The core may occupy all or a part of the space between the bottom surface and the top surface and between the first end portion and second end portion.

The core 102 preferably includes a magnetic shielding material 104 such as a ferromagnetic material. Examples of magnetic shielding material include soft iron, iron-silicon alloys, nickel iron alloys, magnet steel, chromium magnet steels, tungsten magnet steel, cobalt magnet steels, comol, indalloy, remalloy, alnico alloy, ceramic and mu metal. The magnetic shielding materials may comprise one or more sheets/metals and may be attached to the rest of the core using adhesives such as epoxy or by other attachment techniques. In an embodiment of the invention, the magnetic shielding material may be wrapped externally of the remainder of the core. In other embodiments, the metallic shield may be located within a portion of the core.

The core may be rigid or may be constructed using pliant material to allow the positioning of the coil assembly close to the site of an injury. A pliant core or pliant coil is preferably easily shaped or modified to fit the patient. Construction techniques to increase flexibility of materials are known to those skilled in the art. For example, to increase flexibility, single stranded wires may be replaced with multiple stranded wires and solid cores may be replaced with multiple sheets of thinner material.

Coil

The coil 103 may be formed by wrapping multiple turns of an electrically conductive wire around an axis tangential to the plane of the core to form a multi-loop coil. Each loop preferably has at least two dimensions wherein a first dimension is at least 5 times as great as a second dimension. The wire may be insulated or uninsulated and of between about 10 to about 40 gauge, preferably between about 20 and about 40 gauge, more preferably between about 24 to about 36 gauge. Uninsulated wires may be used to form the coil if measures are taken to prevent electric contact and short circuit along the length of the wire. Such measures may comprise, for example, a non-conductive core with grooves, channel or conduits on the surface.

Other methods of fabricating both the coil and the core, such as printed circuit technology (i.e., single and multiple layered printed circuit board) and semiconductor fabrication technology, may also be used to fabricate the coil. Many additional circuit elements may be added to a printed circuit to alter the electrical characteristics of the coil. Examples of circuit elements that may be included in the printed circuit coil include any active and passive elements which can be fabricated using printed circuit technology such as resistors, capacitors, diodes and transistors.

The coil may have a sufficient number of turns to have an inductance of between about 60 milli-Henrys to about 200 milli-Henrys, preferably between about 80 milli-Henrys to about 140 milli-Henrys and most preferably between about 100 milli-Henrys to about 120 milli-Henrys. The electrical resistance of the coil is preferably between about 1 ohm to about 200 ohms, preferably between about 10 ohms to about 150 ohms, such as between about 40 and about 100 ohms, and most preferably between about 60 ohms and about 80 ohms. The coil may further be connected in parallel to a capacitor to form an inductor-capacitor (LC) circuit with a Q factor of about 2.0 to about 6.0. In a LC circuit the coil behaves as an inductor and is represented by the symbol L and the capacitor is represented by the symbol C.

The electrical characteristics of the "planar" coil of the present invention, such as, for example, the inductance, resistance, capacitance and Q factor, may be adjusted by the electrical connection of additional inductors, capacitors and resistors to the coil. Thus, in situations where the electrical characteristics, such as the Q factor, are altered beyond a preferred range, the electrical characteristics may be restored to the desirable range by the addition of active or passive electronic elements. Passive or active elements which may be added to the coils include inductors, resistors, capacitors, operational amplifiers, and emitter followers, cores and the like. The elements may be electrically connected in parallel or in series. For some elements, such as a core or an inductor designed to produce cross inductance with the coil, no direct electrical connection may be necessary. The inductive capacity of the core may be adjusted, for example, by introduction or removal of ferromagnetic material to the core. Alternatively, inductors may be positioned adjacent to the coil to induce cross inductance.

PEMF Treatment

In accordance with another aspect of the invention, the invention is directed to a method for applying an electromagnetic field to a patient. One or more PEMF coil is applied to an injured area of a patient's body. A periodic electric current is conducted through the one or more coils to generate a PEMF. If more than one PEMF coil is used, the location of the coils and the timing of the pulsed electromagnetic fields may be adjusted to provide an additive PEMF at the site of injury. For treatment, the PEMF applied may be of North or South polarity. One preferred method of PEMF treatment is to position the North polarity adjacent to the injured area of a patient. Alternately, multiple coils may be positioned to provide maximal coverage of an injury site. A static magnetic field may optionally be applied to the affected area. The static magnetic field may be supplied by a permanently magnetized core of the coil or it may be supplied by applying a constant current through the coil.

During treatment, the coil may be attached to a patient using a number of methods, such as, for example, adhesives, elastic bandages and hook and loop (or Velcro™) fasteners. Furthermore, the coil may comprise additional means such as an electrical resistance coil or a chemical heat pack to provide heat to the injured area.

The periodic electric current may be a non-inverting current in the form of square waves, sawtooth waves, triangle waves, DC-biased sinusoidal waves, rectified sinusoidal waves or a combination thereof. The non-inverting current, in turn, generates a non-inverting electromagnetic field on the therapeutic coil.

One example of a suitable periodic electric current comprises a plurality of pulses, each pulse having a sine wave shape with no abrupt current changes. The pulses may be delivered at a rate of about 1.0 pulses to about 500 pulses per second. The frequency of the periodic wave may be chosen to correspond to the cyclotron resonance frequency of a pre-selected ion such as, for example, copper, silver, gadolinium, potassium, chloride, zinc, cobalt, iron, manganese, sodium, calcium, magnesium and lithium ions. Injuries treatable by this method include soft tissue injuries such as strains, sprains, contusions, edemas, thermal and chemical burns, surgical incisions, ulcers, abrasions, skin grafts, nerve grafts, tears, bruises, spinal cord injuries, torn tendons, hernias, rheumatoid arthritis, and osteo-arthritis.

Other injuries which may also be treated include arthritis, broken bones, and fractures.

In another embodiment of the invention, the coil may comprise heating means to provide heat to an area to be treated. Heat may be provided electrically or chemically. Electrical heat may be supplied by providing a current through the coil to produce resistive heat. The resistance of the coil may be changed to optimize heat production. Chemical means, such as an exothermic or endothermic reaction, may be used to either heat or chill an area to be treated. Examples of exothermic and endothermic reactions include, for example, sodium acetate or ammonium nitrile, which when allowed to crystallize from a supersaturated solution or mixed with water can produce heat or cold respectively.

Control Circuit

The control circuit switches electrical power from a power supply to provide a periodic electric current to a PEMF coil. A preferred embodiment of tile control circuit may comprise a solid state switching circuit and a solid state control means for controlling the operation of the solid state switching circuit.

The solid state switching circuit may comprise any solid state switching elements, such as, for example, transistors. Transistors may be of any type including bipolar transistors or field effect transistors. Suitable transistor types may be, for example, power switching, junction gate field effect, insulated gate field effect and metal oxide semiconductor transistors.

The solid state control means may be, for example, an oscillator. Oscillators may comprise for example, operational amplifiers, a timer chip such as the 555 integrated circuit (IC) oscillator or a voltage controlled oscillator. Numerous integrated circuit oscillators are known to those skilled in the art such as, for example, 566, LM331, 8038, 2206, 74LS124, 74LS325–327, 74SI24 and MC4024. Oscillators constructed using these integrated circuits may have a period from several seconds to about 80 megahertz. Alternatively, the oscillator circuit may comprise a crystal oscillator with overtone mode crystals to provide frequencies in excess of about 250 MHz. Further, frequency dividers may be incorporated to reduce the frequency below 10 Hz. In addition, oscillators may be implemented using digital means such as microcontrollers, microprocessors, and microcomputers. The frequency of the oscillators may be adjusted by varying the values of various electronic components following the integrated circuit manufacturer's instructions.

Although the solid state control and switching means were described using discrete electronic elements such as transistors, oscillators and the like, similar solid state control means and switching means can be implemented using other electronic methods such as a microprocessor, a microcomputer, a microcontroller, a gate array, or a specially designed integrated circuit or the like. Further, solid state means such as switches, timers, and oscillators may be substituted with mechanical or electromechanical devices such as switches and the like.

The solid state control means and the solid state switching means may each derive electrical power from a regulated power supply. Regulated power supplies are known to those of skill in the art and may comprise discrete or integrated voltage and current regulators.

An amplifier means may be used between the signal generator and the coil to boost the voltage or current supplied to the therapeutic PEMF coil. The amplifier may be a voltage amplification circuit such as a DC-DC amplifier, a current amplification circuit such as an emitter follower or a combination of both.

An inductor-capacitor (LC) resonant circuit such as the PEMF coil or the PEMF coil connected in parallel with a capacitor typically will oscillate (ring) after a driving pulse is turned off. By tuning the LC circuit to resonance, a 10 volt pulse will produce up to 100 peak volts across the LC circuit. During resonance, currents of large magnitude circulate between L and C, generating strong magnetic fields. This oscillation may cause field inversion, that is, a reversal of the polarity of the electromagnetic wave generated. While a shunt diode, connected in parallel with the LC circuit can prevent field inversion, this method has the undesirable effect of increasing energy consumption.

By the proper adjustment of the frequency and duty cycle of the periodic electric current, the oscillation and field inversion can be eliminated or minimized. To achieve this effect the on period of a periodic electric current may be set sufficiently long to fully charge the capacitor. It is preferable that the off period is of sufficient duration to allow the voltage across the inductor capacitor circuit to decay to a value close to zero. Small negative voltages close to zero may be, for example, between about 0 volts to −0.1 volts, preferably between 0 volts to about −1.0 millivolts and most preferably between 0 volts and −0.5 millivolts. When the low non-negative voltage is reached, the on pulse may again turn on and recharge the capacitor to prevent oscillations of the electromagnetic field into the negative range. One efficient method for powering the PEMF coil is to adjust the frequency of the on and off pulses to match the LC circuit's natural resonant frequency.

To accomplish this energy saving technique, the coil inductance, resistance and capacitance are selected to obtain LC resonant frequency of the desired time period. It is preferred that the duty cycle of the periodic electric current and the LC resonant frequencies coincide.

The PEMF coil may have an adequate number of turns of wire and the proper wire size so that sufficient electromagnetic field will be propagated into the treated tissue. As coil dimensions may be different for each application, the resonating capacitor and periodic electric current may be selected to match the LC characteristics of the coil. For example, a PEMF coil device may have a core dimension of about 3 inches long by about 3 inches wide by about 5/8 inches thick with magnetic shielding metal of about 0.03 inch thickness. A suitable wire for this coil may be a wire of about 28 gauge wound around the core for about 800 turns forming a coil with about 100 milli-Henrys inductance and about 65 ohm resistance. A suitable capacitor for connection to this coil may have a value of about 0.22 microfarads.

Power Supply

The electric power for electromagnetic field generation in the portable PEMF coil may be supplied by electric batteries. Electric batteries may be of any type know to those of skill in the art and may be in the form of a battery pack and may be attached to the PEMF coils to form a single PEMF apparatus. Alternatively the electric batteries may be contained in a separate battery pack and connected to the PEMF coils by a cord. The cord may be connected to the battery pack and the coils by detachable connectors. The detachable connectors may be used to connect one battery pack to multiple PEMF coils or one PEMF coil to multiple battery packs. In addition, detachable connectors may allow the exchange or replacement of depleted battery packs with charged battery packs.

The unregulated power supply, or the regulated power supply, may optionally include a resistor and a zener diode, and a light emitting diode connected between the input voltage and ground for monitoring the voltage supply and generating a signal that indicates when the apparatus is in operation. The power supply may further comprise means for connecting to an external power source to power the PEMF coil, to recharge the batteries, or both. A timing circuit may optionally be incorporated to automatically supply power to the coil for a preset period of time, such as 30 minutes. This timing function sets the treatment period and prevent battery depletion if the user forgets to turn the PEMF coil off.

Other embodiments and advantages of the invention are set forth, in part, in the description which follows and, in part, will be obvious from this description and may be learned from practice of the invention.

EXAMPLE

Example 1
Field Strength Measurement of a Helmholtz Coil

A Helmholtz coil was measured using detectors to determine the magnitude of the generated field. In the initial test a conventional detector was used. Conventional techniques used for measuring the flux from this coil employ a sensor Helmholtz coil. The currents induced in each side of the sensor coil induces currents which are additive to each other. The result is that maximum flux appears to occur at the center of the coil.

Bones are not structured in a coil configuration and thus a coil sensor is not dispositive of the current which would be generated in an elongated member, such as a bone. To determine the field strength a Helmholtz coil may apply to an elongated member such as a human bone, the field was measured a second time using a straight wire sensor. Results from measurements conducted using the straight wire sensor indicates that at the edge of the coils, maximum flux is generated and flux at each side is of opposite polarity.

Measurement using the straight wire detector showed the surprising result that the magnetic field generated by the Helmholtz coil is not concentrated at the center of the coil. Contrary to popular belief, the field generated by a Helmholtz coil is inhomogeneous. That is, each side of the Helmholtz coil induces a DC current of opposite polarity to that induced by the other side. Furthermore, maximum field strengths are generated at the sides of the coil not in the center. Testing indicates that zero magnetic fields (field dropouts) occur at the center of the Helmholtz coil and magnetic fields of opposite polarity are generated at the sides of the coils.

As fields of opposite polarity are generated by Helmholtz coils, DC currents of opposite polarity are generated in bones and tissue. This is not ideal for healing. Ideally, the induced currents are of one polarity and the magnetic fields are homogenous. Furthermore, the flux through the center of a Helmholtz coil is zero. Thus, the center of the Helmholtz coil receives no electromagnetic field.

Example 2
Field Strength Measurement of a PEMF coil According to the Invention

The magnetic flux intensity adjacent to a PEMF coil according to the present invention was measured by a wire sensor. Briefly, a coil was energized using a pulsed signal generator and a wire sensor was swept across the surface. The wire sensor was connected to an oscilloscope for the measurement of magnetic field strength. To measure the magnetic field strength using this wire measuring means, two types of coils, one comprising a magnetic shield and one without a magnetic shield were tested. The location of the magnetic shield is shown in the cross section of the PEMF coil (FIG. 2A). The magnetic shield boosted the field strength of the coil by approximately three fold (FIG. 2C). The magnetic field generated by the coil according to the invention has substantially a constant field strength. Preferably the field is constant in magnitude and non-inverting over a surface of the coil. Measurements across the area of field generation did not detect any substantial inhomogeneities such as sudden increases (spikes) and sudden decreases (dropouts) in field strength. The coil was driven using a signal generator (Example 3) and field strength across the surface of the coil was measured using an oscilloscope. No field inversion was detected across the area of field generation. The top and the bottom surfaces of the coil generated PEMF of opposite polarity. Preferably, the N polarity of the coil is positioned proximal to the surface of a patient to be treated.

The electromagnetic field strengths of a PEMF coil according to the invention and a Helmholtz coil were measured. While the two coils show comparable field strength on the surface of the coil, the core of the invention has less field decay as a function of distance (FIG. 3). As a result, at a distance of about 5 inches from the coils, the inventive coil has a relative field strength about 4 fold higher than the Helmholtz coil Example 3
Signal Generator for Non-Inverting PEMF An efficient non-inverting signal generator was produced to energize a coil without the need for a shunt diode. A schematic of one method of using the signal generator for PEMF treatment is shown in FIG. 4A. Briefly, signal generator 113 designed to deliver pulsed voltage is connected to a 0.22 microfarad capacitor 402 connected in parallel to coil 103. A sensing wire 202 is connected to an oscilloscope 204 by wires 203 for the detection of pulsed electromagnetic fields.

The proper adjustment of the signal generator pulse on and off times is important. Proper pulse timing prevents the LC circuit from ringing, reduces negative inverted currents, and increases electrical efficiency. This also eliminates the need for an energy consuming clamping diode across the LC circuit.

For optimal performance, the frequency of the pulsed signal generator is preferably tuned to have an off time of a duration short enough to prevent voltage inversion and long enough to allow the voltage drop across the coil to proximate zero. Because the electrical characteristics of each coil, such as capacitance, inductance and resistance may be different the frequency of the power cycle may be optimally tuned for each coil.

The overall operation of one embodiment of the signal generator may now be explained by referring to FIG. 5. Switching means, in this case a transistor 501, controls the power supplied to the coil 103. The coil 103 may be part of a coil assembly 101 (FIG. 1). Coil assembly 101 may comprise a core 102 and a coil 103 (FIG. 1). The capacitance of the coil is adjusted by capacitor 402 (FIG. 5). Solid state switching control means 502 controls the voltage and current delivered to the coil 103. The solid state switching control circuit means 502 provides an electric signal which causes transistor 501 to switch between an "off" state and an "on" state. In the off state, the transistor behaves as an open circuit and the battery and the coil is electrically isolated. In the on state, the transistor is in saturation and the battery and the coil is electrically connected.

The first switching control circuit means 502 may be a pulsed oscillator such as a first 555 IC oscillator. This first switching control circuit means is controlled by a second switching control circuit means 512 which may be a pulsed oscillator such as a second 555 IC oscillator. The connection between the first switching control means 502 and the second switching control means 512 may comprise diode 539 to ensure proper current direction and capacitor 537 to ensure proper capacitance. The second switching control circuit means 512 may function as an energy saving device. Energy may be saved, for example, if the second switching control circuit means 512 is set to switch the first switching control circuit means on and off in one second cycles such that the PEMF is only applied about 50% of the time. The first switching control circuit means 502 generates pulse rates optimally of from about 0.5 millisecond on, and about 2–3 milliseconds off. The frequency of the first switching control circuit means 502 and the second switching control circuit means 512 may be adjusted by varying the values of capacitors 511, 515, 535 and 536, resistors 509, 510, 517, 540 and 541 or potentiometers 504 and 505. Diodes 544 and 545 ensure proper current direction for regulation of first switching control circuit means 502.

The first switching control circuit means is powered by a regulated power supply from a voltage regulator 518 to insure accurate timing. Regulated power supply may be provided by a plurality of voltage regulators available commercially as is known to those of skill in the art. Voltage regulator means 518 may be used to provide regulated voltage to the solid state switching control means 502 and 512 to ensure that the frequency of the oscillators will not be changed by fluctuation in supply voltage. Capacitor 531 is connected in parallel with the power supply to stabilize voltage fluctuations. A voltage dropout circuit, comprising capacitor 531 and 534, zener diode 532, resistor 533 and voltage dropout device 513 is connected across the output of the voltage regulator 518. If the output voltage of the voltage regulator drops below a predetermined voltage level, such as for example 10 volts, the voltage dropout device 513 will turn off the circuit. One cause of voltage regulator output drop may be the reduction of voltage output from a depleted battery. The pre-determined voltage level causing the activation of the voltage dropout device 513, may be set by adjusting the value of zener diode 532.

The circuit is optionally supplied with a socket 523, which may be adapted to receive an external power supply for operation of the circuit without batteries, for recharging the battery 522, or for both. Optional diode 521 may be added to prevent damage to the circuit by reversing the polarity of the external power supply. An optional indicator means 520 such as a light emitting diode, is connected in parallel with the coil to indicate operation of the circuit. Current through indicator means 520 may be limited by resistor 538 to prevent damage.

To control the treatment periods, a timing circuit may be connected between the batteries and electronics. One method of implementing a timing circuit is shown in FIG. 5. In FIG. 5, HEX FET 526, resistor 543, 507, capacitor 503, zener diode 542 and diode 530 and switch 506 comprise the timing circuit. A treatment cycle may be started by activating the timing circuit. Timing circuit activation may be performed by the momentary closure of toggle switch 506. Timing period is controlled by resistor 507 and capacitor 503. The HEXFET 526 acts as a solid state on and off device actuated by timing elements capacitor 503 and resistor 507. At the end of the cycle, the power is turned off automatically by the timing circuit. The timing circuit thus limits the treatment time and prevents the discharge of batteries. A treatment period may be set, for example, for about 30 minutes. Treatment times may vary depending on the position of the coil and the nature of the injury to provide optimal results.

In operation, the oscillators of the switching control circuit means 512 and 502 provide power to coil 103 from power supply 522. The duty cycle of switching control circuit means 502 and 512 is adjusted to provide sufficient frequency and duration to energize coil 103 in a non-inverting fashion. Because the voltage of the coil is not allowed to drop below zero, the direction of the current through the coil is non-inverting and the field generated by the non-inverted current is non-inverting.

Other embodiments and uses of the invention will be apparent to those skilled in the art from consideration of the specification and practice of the invention disclosed herein. The specification and examples should be considered exemplary only. The intended scope of the invention is only limited by the claims appended hereto.

I claim:

1. A therapeutic coil for pulsed electromagnetic field comprising, a core having a bottom surface and a top surface defining a thickness, a first side edge portion and a second side edge portion defining a height, and a first end portion and second end portion defining a width; and an electrically conductive wire wound a plurality of turns around the first end portion, the bottom surface, the second end portion and the top surface, to form a coil comprising a plurality of loops, each loop having at least two dimensions wherein a first dimension is at least 5 times as great as a second dimension.

2. The therapeutic coil of claim 1 wherein said core comprises a pliant material shaped to conform to an exterior conformation of a patient's body.

3. The therapeutic coil of claim 1 wherein said core further comprises a magnetic shielding material at least partially disposed between said bottom surface and said top surface.

4. The therapeutic coil of claim 3 wherein said magnetic shielding material is selected from the group consisting of soft iron, iron-silicon alloys, nickel iron alloys, magnet steel, chromium magnet steels, tungsten magnet steel, cobalt magnet steels, comol, indalloy, remalloy, alnico alloy, ceramic, mu metal, and combinations thereof.

5. The therapeutic coil of claim 1 wherein said electrically conductive wire is an insulated wire.

6. The therapeutic coil of claim 1 wherein said electrically conductive wire is between about 18 gauge to about 40 gauge.

7. The therapeutic coil of claim 1, wherein said electrically conductive wire is wound a plurality of turns sufficient to provide said coil with an inductance of between about 80 to about 200 milli-Henrys.

8. The therapeutic coil of claim 1 wherein said coil has an electrical resistance of less than about 100 ohms.

9. The therapeutic coil of claim 1 further comprising a capacitor, electrically connected to said coil in parallel, to form a LC circuit with a Q factor of about 2 to about 5.

10. The therapeutic coil of claim 1, further comprising a fastening means to affix said coil to an affected area of a patient.

11. The therapeutic coil of claim 10, wherein said fastening means is a hook and loop fastener.

12. The therapeutic coil of claim 1 further comprising heating means for applying heat to a body part in proximity to said coil.

13. The therapeutic coil of claim 12 wherein said heating means is an electrical resistance heater.

14. The therapeutic coil of claim 12 wherein said heating means is a chemical heater.

15. A pulsed electromagnetic field generator comprising, a coil comprising one or more core each with a bottom surface and a top surface defining a thickness, a first side edge portion and a second side edge portion defining a height, and a first end portion and second end portion defining a width, and an electrically conductive wire wound a plurality of turns around the first end portion, the bottom surface, the second end portion and the top surface, to form a coil comprising a plurality of loops, each loop having at least two dimensions wherein a first dimension is at least 5 times as great as a second dimension;

a battery for applying a current said coil to generate said magnetic field; a solid state switching circuit connected between said battery and said PEMF coil for controlling current flow from said battery to said coil; and control circuit means connected to said solid state switching circuit for operating said solid state switching circuit at a frequency to prevent an inversion of the magnetic field.

16. The pulsed electromagnetic field generator of claim 15 said generator being portable.

17. The pulsed electromagnetic field generator of claim 15, wherein said control circuit means comprises an oscillator circuit.

18. The pulsed electromagnetic field generator of claim 17, wherein said oscillator circuit comprises at least one 555 timer chips.

19. The pulsed electromagnetic field generator of claim 15, wherein said control circuit means comprise a microcontroller circuit.

20. The pulsed electromagnetic field generator of claim 15 further comprising a regulated power supply having a ground, an unregulated input, and a regulated output connection for supplying regulated power to said control circuit means, said ground connected to a ground terminal of said battery, said unregulated input connected to a positive terminal of said battery, and said output connected to a power input of said control circuit means.

21. The regulated power supply of claim 20 further comprising a resistor and a zener diode, and a light emitting diode connected between the unregulated input and ground of the regulated power supply for monitoring voltage supply and generating a signal indicative of when the apparatus is in operation.

22. The pulsed electromagnetic field generator of claim 15 further comprising means for connecting an external power source to said circuit.

23. The pulsed electromagnetic field generator of claim 15 further comprising automatic shutoff means to limit operation of said pulsed electromagnetic field generator for about 10 to about 60 minutes.

\* \* \* \* \*